United States Patent
Kato et al.

(10) Patent No.: US 6,479,992 B2
(45) Date of Patent: Nov. 12, 2002

(54) LEAKAGE FLUX FLAW DETECTING METHOD AND METHOD FOR MANUFACTURING HOT ROLLED STEEL SHEET USING THE SAME

(75) Inventors: Hiriharu Kato, Yokohama (JP); Junichi Yotsuji, Yokohama (JP); Akio Nagamune, Machida (JP)

(73) Assignee: NKK Corporation, Tokyo (JP)

(\*) Notice: Subject to any disclaimer, the term of this patent is extended or adjusted under 35 U.S.C. 154(b) by 0 days.

(21) Appl. No.: 10/040,682

(22) Filed: Jan. 7, 2002

(65) Prior Publication Data
US 2002/0121896 A1 Sep. 5, 2002

Related U.S. Application Data

(63) Continuation of application No. PCT/JP00/04645, filed on Jul. 12, 2000.

(51) Int. Cl.[7] .............................................. G01N 27/83
(52) U.S. Cl. ....................... 324/232; 72/11.1; 148/111; 324/238
(58) Field of Search ................. 324/232, 238; 72/11.1–11.3; 148/111; 219/602, 619

(56) References Cited

U.S. PATENT DOCUMENTS

| | | | |
|---|---|---|---|
| 4,477,776 A | | 10/1984 | Spierer |
| 4,727,321 A | * | 2/1988 | Huschelrath ................ 324/226 |
| 4,789,827 A | | 12/1988 | Bergander |
| 4,835,470 A | * | 5/1989 | Novikov et al. ............ 324/220 |
| 5,293,117 A | * | 3/1994 | Hwang ........................ 324/213 |
| 5,414,353 A | * | 5/1995 | Weischedel ................. 324/232 |
| 5,512,821 A | * | 4/1996 | Ando et al. ................. 324/225 |
| 5,739,685 A | | 4/1998 | Suzuma |
| 6,266,983 B1 | * | 7/2001 | Takada et al. ................ 72/11.1 |
| 6,316,937 B1 | * | 11/2001 | Edens ......................... 324/220 |

FOREIGN PATENT DOCUMENTS

| | | | | |
|---|---|---|---|---|
| JP | 57-108656 A | | 7/1982 | |
| JP | 59-214757 | * | 12/1984 | .......... G01N/27/82 |
| JP | 63-065361 | * | 3/1988 | .......... G01N/27/90 |
| JP | 01-21348 | * | 1/1989 | .......... G01N/27/83 |
| JP | 1-209356 A | | 8/1989 | |
| JP | 06-123730 | * | 5/1994 | .......... G01N/27/82 |
| JP | 8-68778 A | | 3/1996 | |
| JP | 8-193980 A | | 7/1996 | |
| JP | 9-145679 A | | 6/1997 | |
| JP | 9-274016 A | | 10/1997 | |
| JP | 10-288603 A | | 10/1998 | |

\* cited by examiner

*Primary Examiner*—Edward Lefkowitz
*Assistant Examiner*—Darrell Hinder
(74) *Attorney, Agent, or Firm*—Frishauf, Holtz, Goodman & Chick, P.C.

(57) ABSTRACT

The present invention provides a leakage flux flaw detecting method in which a ferromagnetic substance such as a steel sheet or coil is magnetized by a plurality of magnetic fields with different intensity and magnetic flux leaking from the ferromagnetic substance having been magnetized is detected by a magnetic sensor, and output signals of the magnetic sensor after the detection of leakage flux are processed so that a signal caused by a flaw in the ferromagnetic substance is highlighted. Since this leakage flux flaw detecting method makes it possible to detect flaws with high accuracy, a scaled or descaled hot rolled steel sheet or coil in which the accurate flaw information such as location, density, size, and the like is known can be provided by applying this method to the manufacturing of hot rolled steel sheet or coil.

46 Claims, 15 Drawing Sheets

LEAKAGE FLUX FLAW DETECTING METHOD AND METHOD FOR MANUFACTURING HOT ROLLED STEEL SHEET USING THE SAME

This application is a continuation application of International Application PCT/JP00/04645 (not published in English) filed Jul. 12, 2000.

BACKGROUND OF THE INVENTION

1. Field of the Invention

The present invention relates to a leakage flux flaw detecting method in which a magnetic field is applied to a ferromagnetic substance to detect magnetic flux leaking from the ferromagnetic substance, by which flaws such as inclusions present in the ferromagnetic substance are detected, and a method for manufacturing a hot rolled steel sheet or a descaled steel sheet using the leakage flux flaw detecting method.

2. Description of Related Arts

As a method for detecting flaws such as inclusions present in a ferromagnetic substance such as a steel sheet, a leakage flux flaw detecting method has widely been used.

As one example, FIG. 1 shows a configuration of a magnetic flaw detector using a magnetic sensor incorporated in a steel sheet inspection line. A magnetic flaw detector 4 is disposed along a transferring path for a steel sheet 1 (ferromagnetic substance) transferred on a product inspection line at a substantially constant speed V by transferring rollers 2 and 3. The magnetic flaw detector 4 includes a magnetizer 5 for magnetizing the running steel sheet 1, a magnetic sensor 6 disposed at a position opposed to the magnetizer 5 so that the steel sheet 1 passes therebetween, and a signal processing unit 7 for processing output signals sent from the magnetic sensor 6.

If a flaw 8 exists in the steel sheet 1 when the steel sheet 1 is magnetized by the magnetizer 5, magnetic flux passing through the interior of the steel sheet 1 is disturbed by the flaw 8, and some of the magnetic flux leaks to the outside of the steel sheet 1. This leakage flux is detected by the magnetic sensor 6, and an output signal sent from the magnetic sensor 6 is processed, by which the flaw 8 can be detected. Also, since the intensity of the leakage flux depends on the size of the flaw 8, the size of the flaw 8 can also be evaluated by the output signal level of the magnetic sensor 6.

On the other hand, the leakage flux detected by the magnetic sensor includes, in addition to the leakage flux caused by a flaw, disturbance of leakage flux caused by nonuniformity of local magnetic characteristics of the steel sheet (nonuniformity of thickness of oxide scale, irregularities of oxide scale/ground steel interface, and the like) or surface roughness. Such disturbance of magnetic flux is unnecessary magnetic flux or noise from the viewpoint of flaw detection.

In order to exclude the influence of such noise, a method, described below, is sometimes used which uses different frequency characteristics of the output signal caused by a flaw (hereinafter referred to as a flaw signal) and the output signal caused by noise (hereinafter referred to as a noise signal).

FIG. 2 shows an example of frequency characteristics of flaw signal and noise signal measured when a steel sheet runs at a constant speed. Generally, as shown in FIG. 2, the flaw signal has higher frequency distribution than the noise signal. Therefore, the flaw signal can be highlighted relatively and extracted by incorporating a bypass filter with a cut-off frequency f in the signal processing unit. Also, a method using a filter having a proper constant to enhance the flaw detecting ability in the leakage flux flaw detecting method has been disclosed in Unexamined Japanese Utility Model Publication No. 61-119760.

However, as shown in FIG. 2, the frequency characteristics of the flaw signal and the noise signal overlap partially. Therefore, in the case where the flaw is minute or the noise is much, even if the bypass filter is provided to discriminate the flaw signal from the noise signal by means of frequency, it is difficult to exclude the influence of noise to a degree such that a flaw can be detected with high accuracy.

SUMMARY OF THE INVENTION

An object of the present invention is to provide a leakage flux flaw detecting method that is capable of detecting flaws even if the flaws are minute or unnecessary magnetic flux or noise is much and a method for manufacturing a hot rolled steel sheet using the leakage flux flaw detecting method.

The above object is achieved by a leakage flux flaw detecting method comprising the steps of: magnetizing a ferromagnetic substance successively to a plurality of different intensities of magnetization; detecting magnetic flux leaking from the same position of the ferromagnetic substance having been magnetized to each of the intensities of magnetization by using a magnetic sensor; and processing output signals of the magnetic sensor corresponding to each of the intensities of magnetization so that a signal caused by a flaw in the ferromagnetic substance is highlighted. Also, a leakage flux flaw detecting method can be used which comprising the steps of: magnetizing a ferromagnetic substance by one or a plurality of magnetizers; detecting magnetic flux leaking from the same position of the ferromagnetic substance having been magnetized successively by a plurality of magnetic sensors provided at positions where the intensity of magnetization is different while the ferromagnetic substance is moved along the magnetic sensors; and processing output signals of the magnetic sensors so that a signal caused by a flaw in the ferromagnetic substance is highlighted.

Also, a hot rolled steel sheet covered with oxide scales or a descaled hot rolled steel sheet in which accurate flaw information such as flaw location and density is known can be manufactured by using a method for manufacturing a hot rolled steel sheet, comprising the steps of: performing hot rolling; detecting flaws in the hot rolled steel sheet by using the above described leakage flux flaw detecting method in accordance with the present invention; and determining the information of the detected flaws.

DETAILED DESCRIPTION OF THE INVENTION

Figure 3:
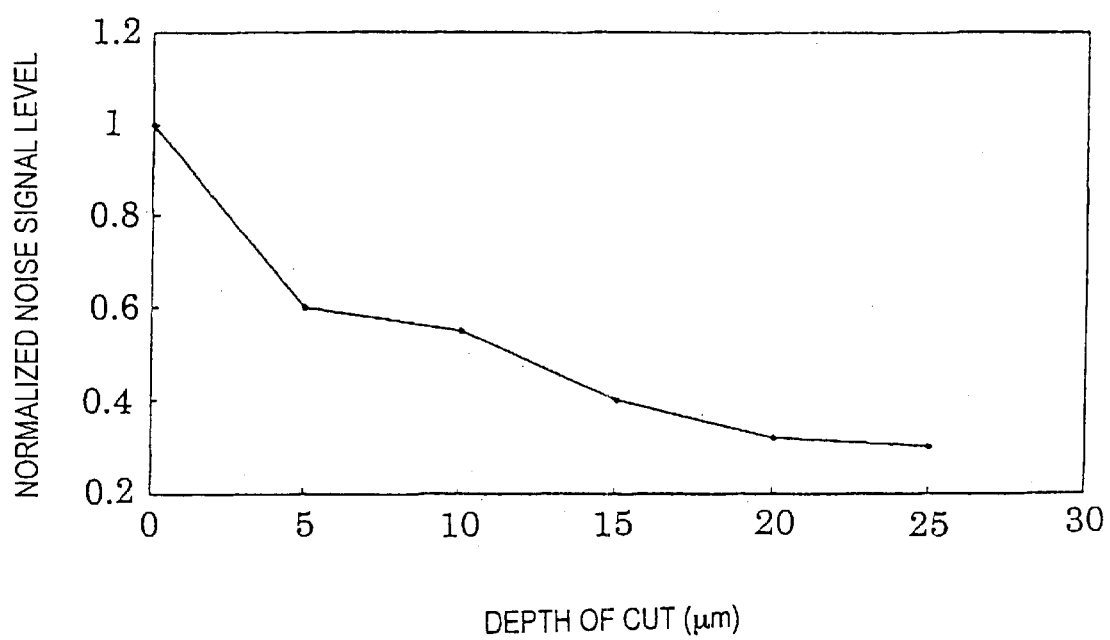
FIG. 3 is a graph showing a relationship between depth of cut and normalized noise signal level.

FIG. 3 shows a measurement result for a noise signal obtained when a steel sheet with a thickness of 1 mm is chemically cut little by little from the surface while paying attention to the prevention of distortion. The noise signal level shown in FIG. 3 is normalized with the signal level before cutting.

The noise signal level decreases gradually as the depth of cut increases, and becomes a half or lower of the level before cutting and stabilizes when the sheet is cut by about 20 $\mu$m. This result is thought to be based on the fact that the influence of nonuniformity of magnetic characteristics of the surface layer caused by surface roughness or cooling of sheet from the surface during manufacture is decreased by the cutting. Such a phenomenon has been confirmed on another steel sheet, and it can be said that a noise source mainly lies in the surface layer of a ferromagnetic substance. On the other hand, flaws such as inclusions generally exists in the interior in almost all cases.

The inventors paid attention to a phenomenon that the magnetic shield effect of a ferromagnetic substance depends on the intensity of magnetization, and examined the magnetic shield effect of a steel sheet existing between a magnetic sensor and flaws or noise sources upon a flaw signal and a noise signal when the steel sheet is magnetized with a different magnetic field by using a magnetizer.

Figure 4:
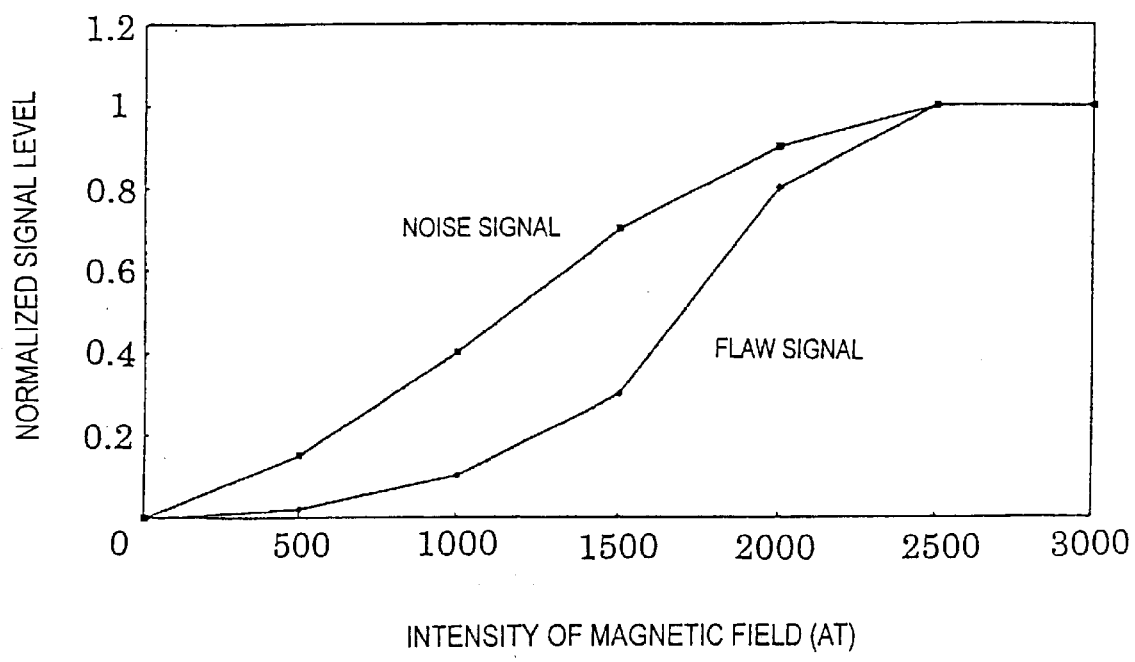
FIG. 4 is a graph showing a relationship between intensity of magnetic field and signal level of flaw signal and noise signal.

FIG. 4 shows a relationship between the intensity of magnetic field and the signal level of flaw signal and noise signal. The signal level shown in FIG. 4 is normalized with the signal level provided when the steel sheet is magnetically saturated with an intensity of magnetic field of 2500 AT or higher.

It is found that when the intensity of magnetic field is decreased from 2500 AT, which is the intensity of magnetic field at which the steel sheet is magnetically saturated, both of the flaw signal level and the noise signal level decrease, and the degree of decrease in the flaw signal level is larger than that in the noise signal level. This phenomenon can be understood as described below.

When the steel sheet is magnetically saturated, the differential relative permeability takes a value close to 1, and the magnetic shield effect is eliminated, so that a level difference between the flaw signal and the noise signal depends on only a distance between the magnetic sensor and a flaw or a noise source. On the other hand, when the intensity of magnetic field is decreased to make the steel sheet unsaturated magnetically, the differential relative permeability takes a value larger than 1, and the magnetic shield effect of the steel sheet appears. At this time, the flaw signal caused by a flaw existing farther from the magnetic sensor is subjected to a stronger influence of the magnetic shield effect than the noise signal coming from the surface layer because the thickness of steel sheet lying between the magnetic sensor and the flaw is large, so that the flaw signal level decreases greatly.

Therefore, if a ferromagnetic substance such as a steel sheet is magnetized to a plurality of different intensities of magnetization, magnetic flux leaking from the ferromagnetic substance is detected by the magnetic sensor, and processing is performed so that a noise signal with a relatively high level is cancelled and a flaw signal is highlighted relatively with respect to the output signal of the magnetic sensor corresponding to each intensity of magnetization, flaws can be detected with high accuracy even if the flaws are minute or the noise is much.

At this time, if, of the plural different intensities of magnetization, the highest intensity of magnetization is set at the intensity of magnetization at which a ferromagnetic substance is magnetically saturated, that is, the differential relative permeability of the ferromagnetic substance is 1, flaws can be detected more effectively.

Also, if a ferromagnetic substance is magnetized to two kinds of intensities of magnetization, and the output signal of the magnetic sensor corresponding to the lower intensity of magnetization is deducted from the output signal of the magnetic sensor corresponding to the higher intensity of magnetization by weighting, the flaw signal can be highlighted more simply and effectively. In this case, as described above, it is preferable that the higher intensity of magnetization be set at the intensity of magnetization at which the ferromagnetic substance is magnetically saturated. In addition, when a ratio of the output of the magnetic sensor corresponding to the lower intensity of magnetization to the output of the magnetic sensor corresponding to the higher intensity of magnetization is calculated, it is found that a high calculated ratio represents a flaw existing close to the surface and a low calculated ratio represents a flaw existing in the interior. By using a proper function, the depth of flaw from the surface can be calculated.

Figure 5:
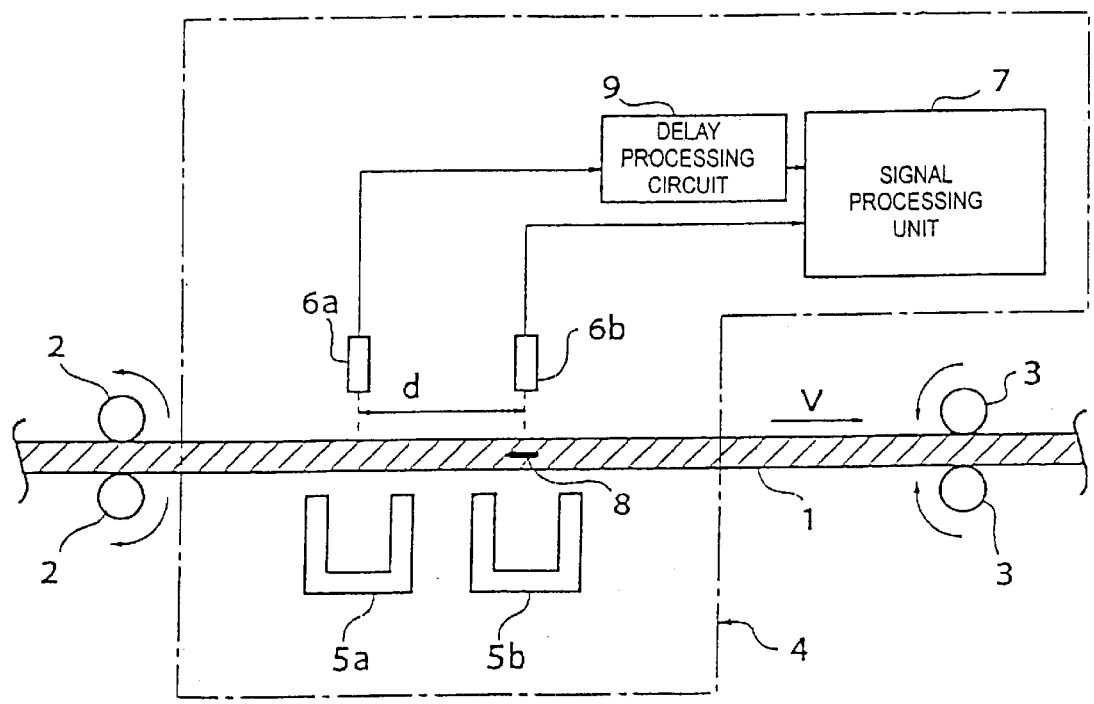
FIG. 5 is a schematic view showing one example of a magnetic flaw detector for carrying out the leakage flux flaw detecting method in accordance with the present invention.

FIG. 5 shows one example of a magnetic flaw detector for carrying out the leakage flux flaw detecting method in accordance with the present invention. In this detector, in addition to a magnetizer 5a and a magnetic sensor 6a provided in the conventional detector shown in FIG. 1, another set of a magnetizer 5b and a magnetic sensor 6b are provided at a distance d from the magnetizer 5a and the magnetic sensor 6a in the running direction of a steel sheet 1. In this embodiment, distances from the steel sheet 1 to the magnetic sensors 6a and 6b, that is, liftoffs L are set so as to be equal.

First, the steel sheet 1 is magnetized by the magnetizer 5a so as to be saturated magnetically, and the steel sheet 1 is magnetized by the magnetizer 5b so as to be unsaturated magnetically. Next, leakage flux from the same portion of the steel sheet 1 is detected by the magnetic sensors 6a and 6b while the steel sheet 1 is moved along from the magnetizer 5a to the magnetizer 5b. Finally, the output signal Vb(t) of the magnetic sensor 6b is deducted from the output signal Va(t) of the magnetic sensor 6a by weighting Vb(t) by $K_2$ using a signal processing unit 7 so that A in the following equation (1) is close to 0 at a position where a flaw 8 does not exist. By this method, a noise signal can be reduced, and the S/N ratio of flaw signal can be increased.

$$A = K_1 \cdot (Va - K_2 \cdot Vb) \quad (1)$$

At this time, by using a delay processing circuit 9, the output signal Va(t) of the magnetic sensor 6a is relatively delayed with respect to the output signal Vb(t) of the magnetic sensor 6b by using a time difference Δt corresponding to the same steel sheet position obtained by dividing the distance or the positional shift d between the magnetic sensors 6a and 6b by a successively measured steel sheet speed V, so that Va(t−Δt) corresponds to Vb(t). Also, the output signals Va(t−Δt) and Vb(t) are filtered by a band-pass filter of 1 to 2 kHz to decrease a direct current noise component and a ground noise component with a low frequency and to cut an electrical noise higher than the flaw signal frequency. The deduction, delay processing, filtering, and the like of output signal may be accomplished with analog signal, but they can be accomplished with digital signal by making analog-digital conversion at a sampling frequency of, for example, 20 kHz.

The liftoffs L of the magnetic sensors 6a and 6b need not necessarily be equal. Also, in order to magnetize a ferromagnetic substance differently, a plurality of magnetizers and magnetic sensors need not necessarily be used, and a set of magnetizer and magnetic sensor may be used and the electric current of the magnetizer may be changed to change the intensity of magnetization.

Instead of magnetizing a ferromagnetic substance to a plurality of different intensities of magnetization as described above, the ferromagnetic substance may be magnetized under a given magnetizing condition by a magnetizer, and magnetic flux leaking from the ferromagnetic substance may be detected by a plurality of magnetic sensors provided at different positions along the magnetization direction with the same effect as described below.

Figure 6:
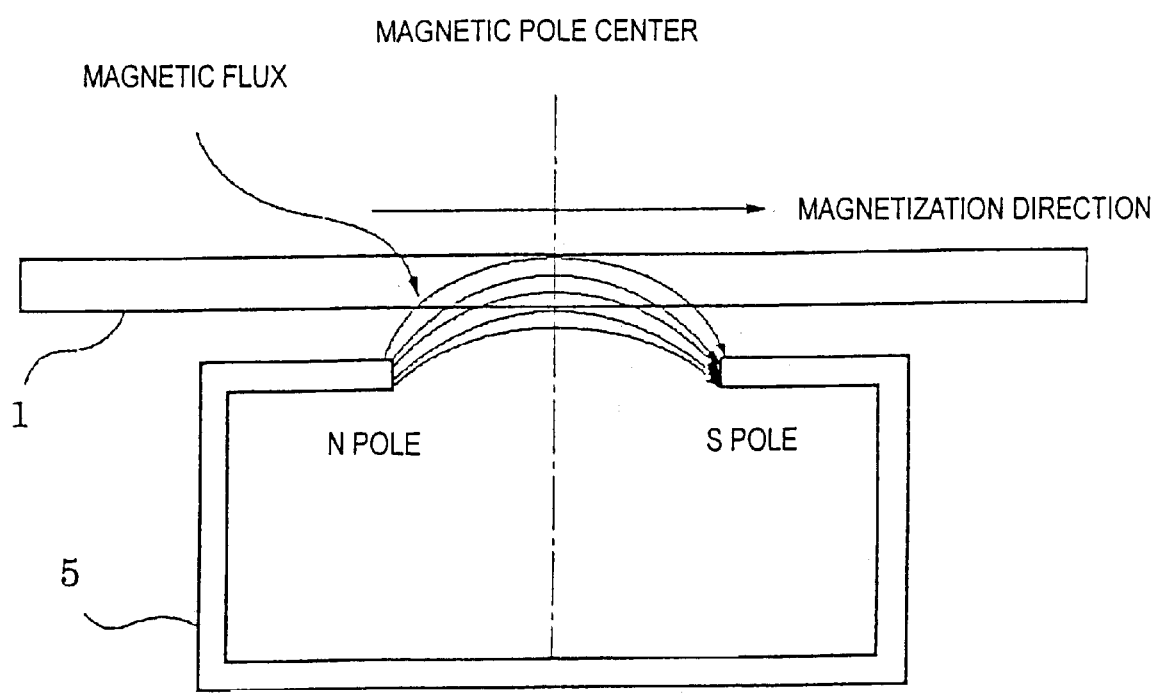
FIG. 6 is a view showing a flow of magnetic flux when a steel sheet is magnetized by using a magnetizer.

FIG. 6 shows a flow of magnetic flux when a steel sheet is magnetized by using a magnetizer.

Some of magnetic flux coming out of the N pole of a magnetizer 5 passes through the steel sheet 1, and magnetizes the steel sheet 1. The quantity of magnetic flux supplied from the magnetizer 5 to the steel sheet 1 increases toward the magnetic pole center of the magnetizer 5, and becomes at a maximum at the magnetic pole center. Therefore, the intensity of magnetization of the steel sheet 1 also becomes at the maximum at the magnetic pole center, and decreases at a position farther from the magnetic pole center. For this reason, if a ferromagnetic substance is magnetized under a given magnetizing condition by a magnetizer, and the leakage flux is detected by a plurality of magnetic sensors provided at different positions along the magnetization direction, the same effect as that obtained in the case where the ferromagnetic substance is magnetized to a plurality of different intensities of magnetization can be achieved.

Figure 1:
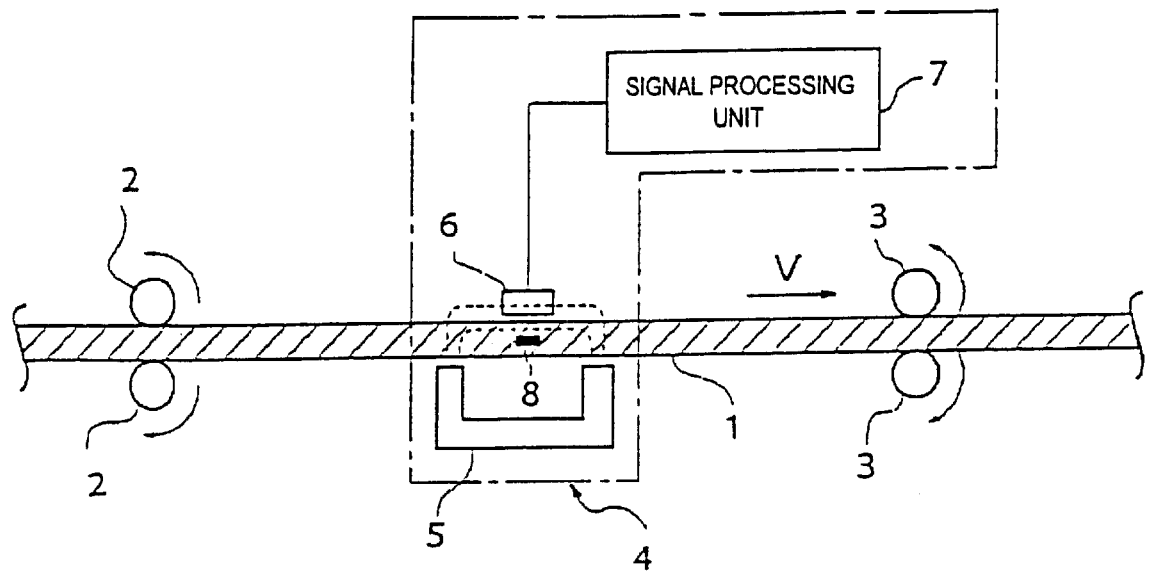
FIG. 1 is a schematic view showing a configuration of a conventional magnetic flaw detector.
Figure 2:
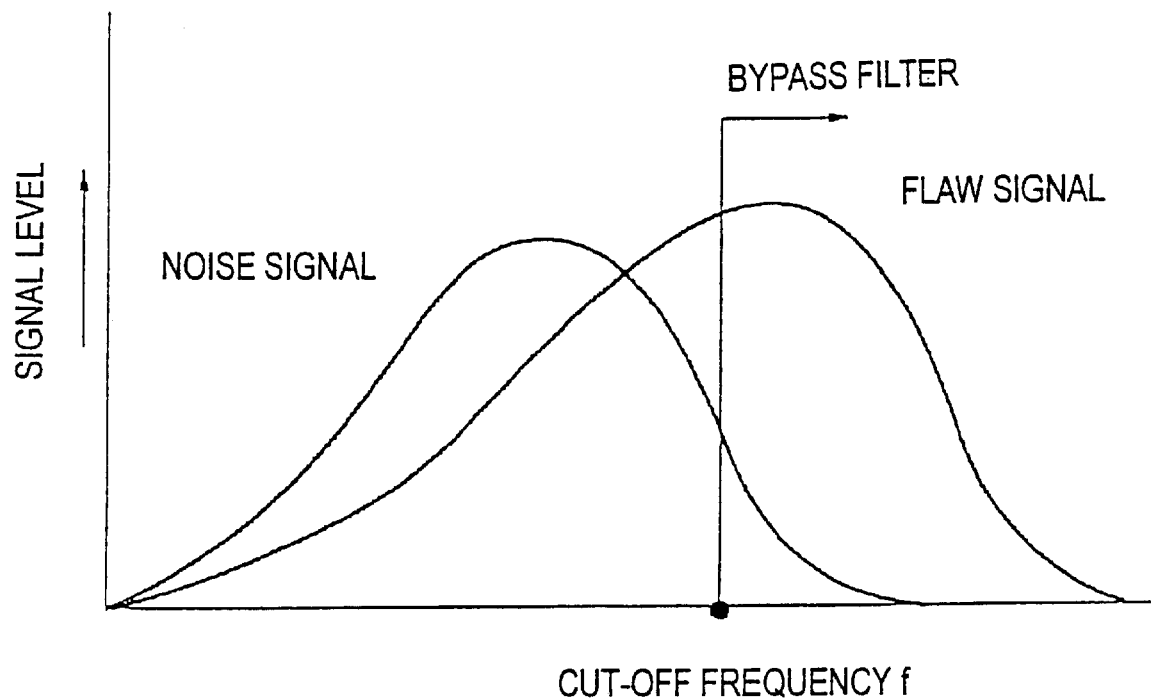
FIG. 2 is a graph showing one example of frequency characteristics of a flaw signal and a noise signal.
Figure 7:
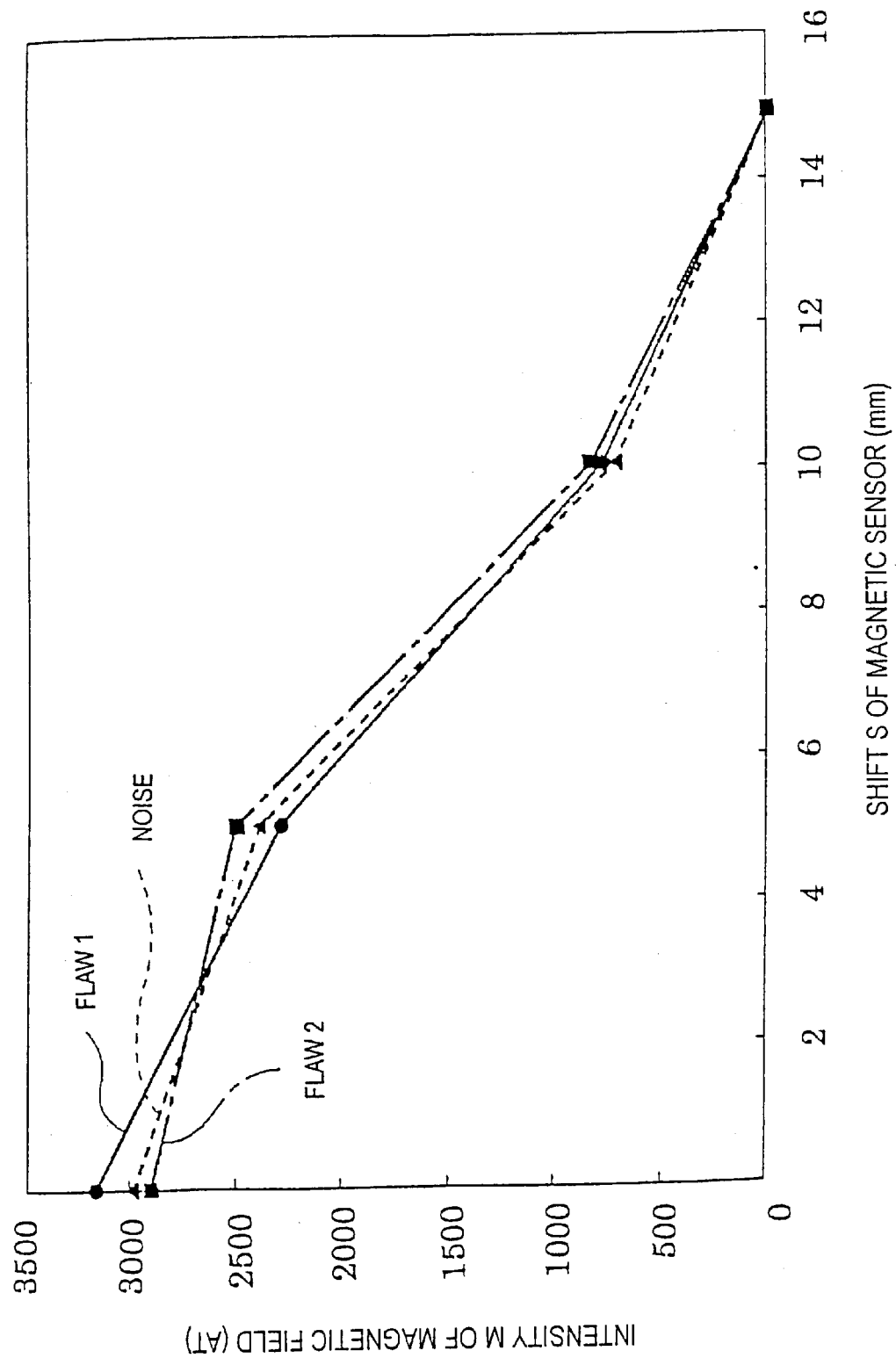
FIG. 7 is a graph showing a relationship between intensity M of magnetic field and shift S of magnetic sensor when the same output signal level is provided.

FIG. 7 shows a result of relationship between the intensity M of magnetic field and the shift S of magnetic sensor obtained for two kinds of flaws and noise existing in the steel sheet 1 with a thickness of 1 mm by using the magnetic flaw detector shown in FIG. 1. This relationship is obtained in a case where the output signal level obtained by changing the intensity M of magnetic field applied by the magnetizer 5 while the position of the magnetic sensor 6 is fixed at the magnetic pole center and the output signal level obtained by inversely fixing the intensity M of magnetic field applied by the magnetizer 5 while the magnetic sensor 6 is shifted by S in the magnetization direction from the magnetic pole center of the magnetizer 5 are equal. At this time, the steel sheet 1 was transferred at a speed of 300 m/min with a liftoff of 1 mm, and was magnetized by the magnetizer 5 with a magnetic pole gap of 12 mm located at a position of 4 mm distant from the steel sheet 1. In the test in which the magnetic sensor 6 is shifted from the magnetic pole center, the intensity M of the applied magnetic field was fixed at 3000 AT. It is found that for a flaw 2 shown in FIG. 7, for example, the output signal level obtained when the magnetic sensor 6 is located at the magnetic pole center and a magnetic field of 2500 AT is applied and the output signal level obtained when the magnetic sensor 6 is located at a position of S=5 mm and a magnetic field of 3000 AT is applied are equal.

As shown in FIG. 7, the data of two kinds of flaws and noise overlap substantially, so that the validity of measurement made by shifting the magnetic sensor 6 in the magnetization direction from the magnetic pole center of the magnetizer 5 can be confirmed.

Thus, with the method in which a ferromagnetic substance is magnetized under a given magnetizing condition by using a magnetizer, and the magnetic flux leaking from the ferromagnetic substance is detected by a plurality of magnetic sensors provided at different positions along the magnetization direction, measurement can be made at a time by using one magnetizer. Therefore, the system configuration is simple as compared with the case where magnetizers are provided for each magnetizing condition. Also, since the magnetizing condition can be changed by one magnetizer, high-speed measurement can be made as compared with the case where measurement is made a plurality of times.

Figure 13:
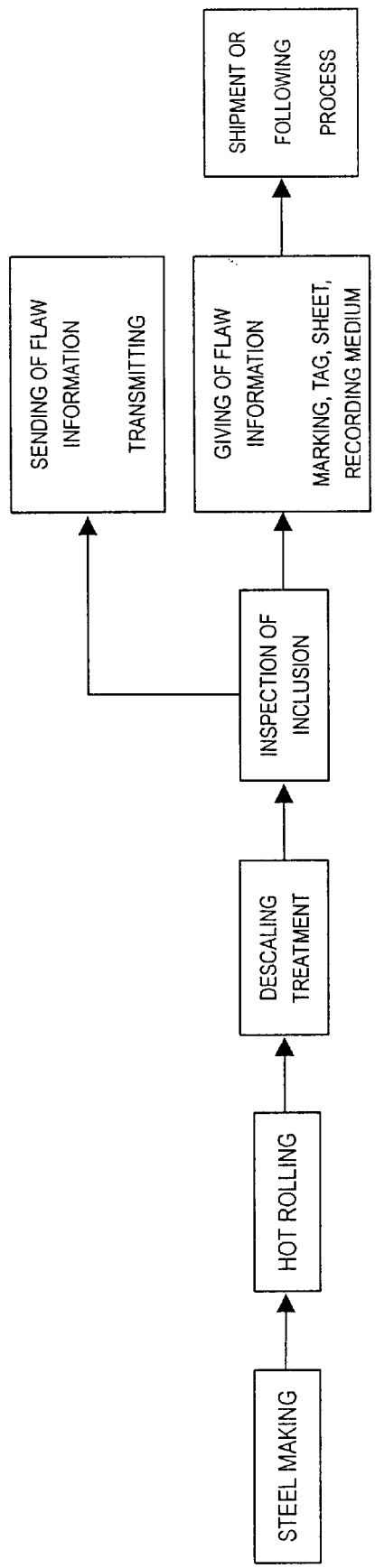
FIG. 13 is a flow diagram showing another manufacturing process for a hot rolled steel sheet, the process incorporating a leakage flux flaw detecting method in accordance with the present invention.
Figure 14:
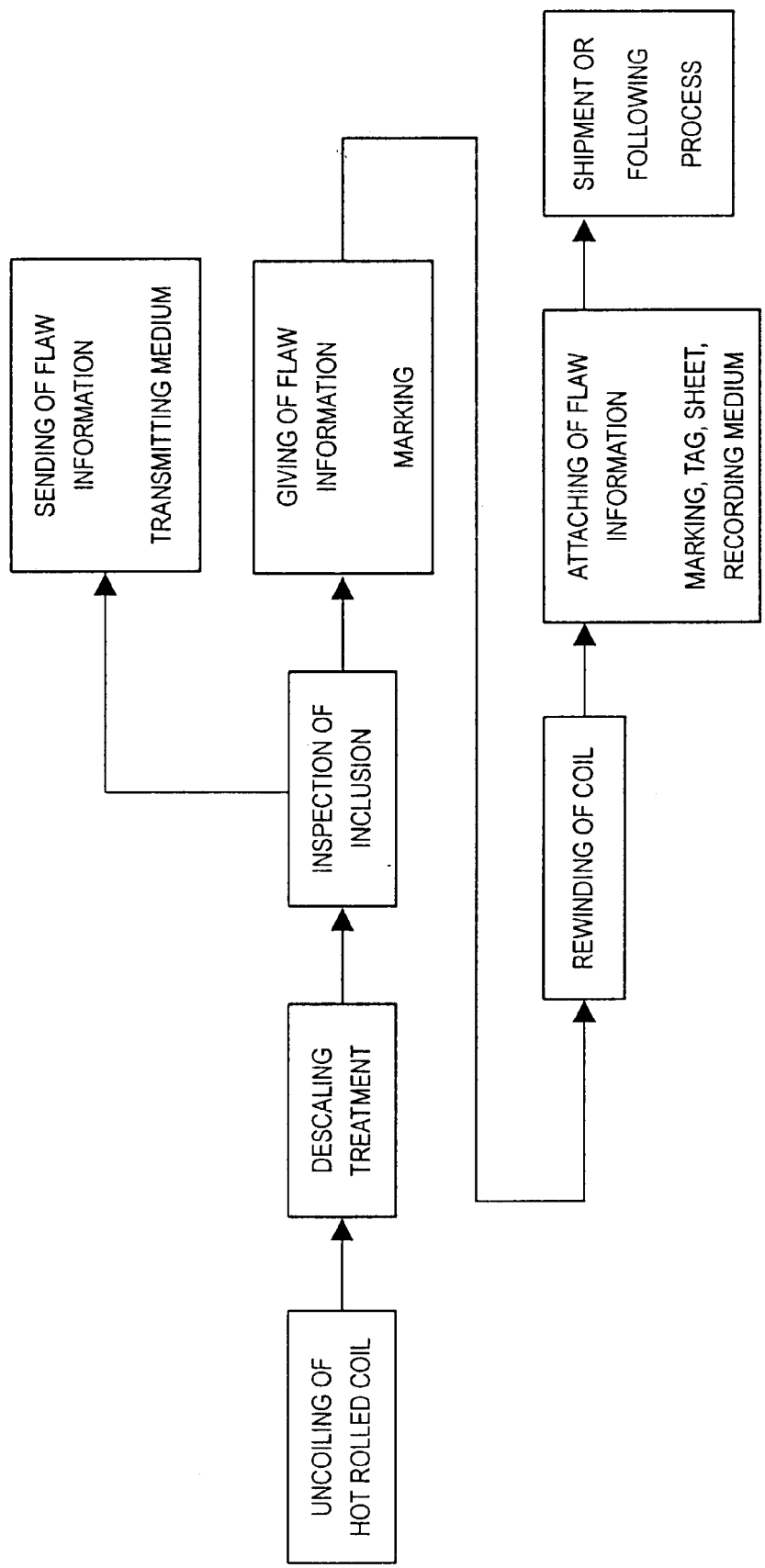
FIG. 14 is a flow diagram showing a manufacturing process for a hot rolled steel coil, the process incorporating a leakage flux flaw detecting method in accordance with the present invention.
Figure 15:
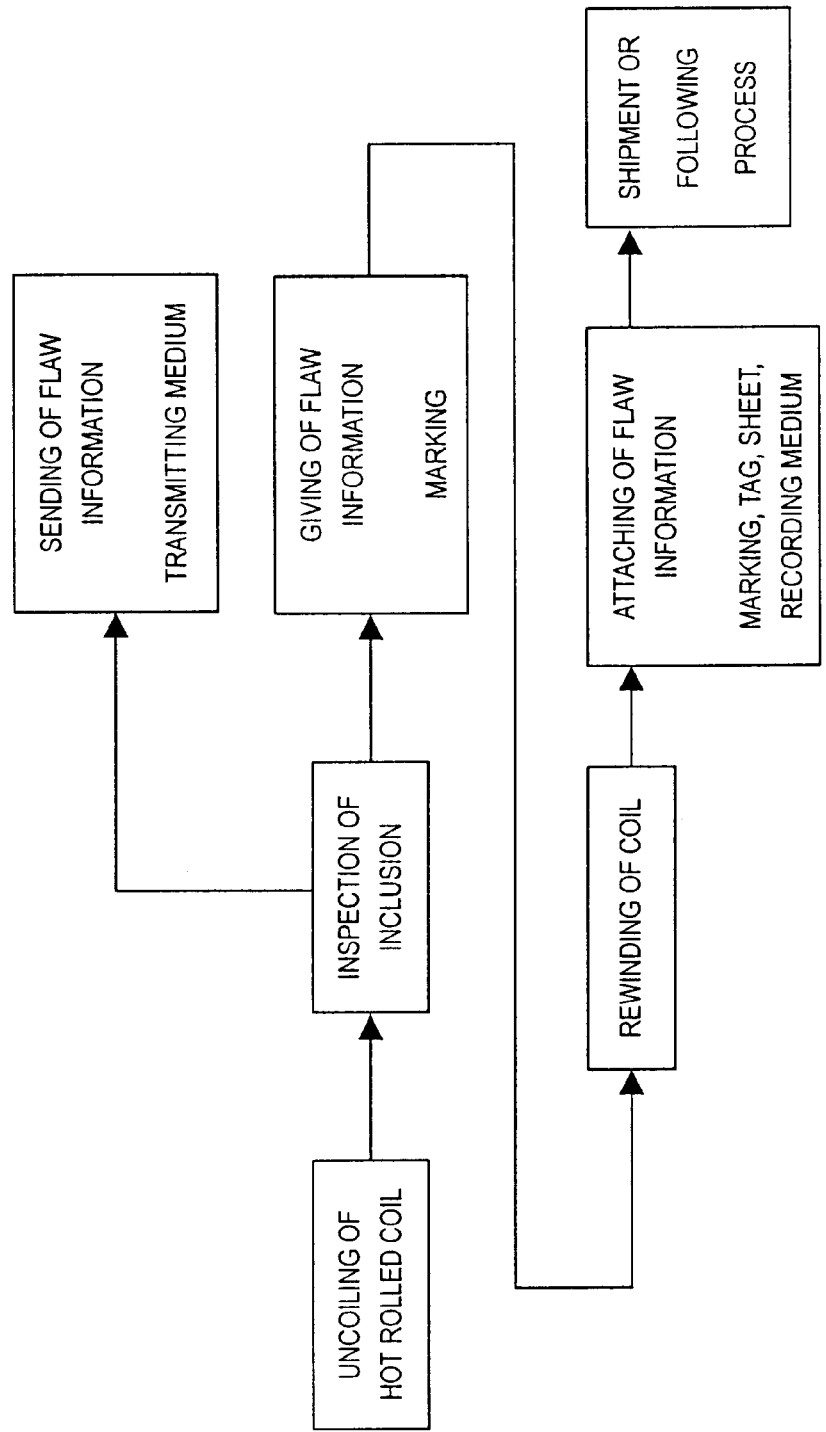
FIG. 15 is a flow diagram showing another manufacturing process for a hot rolled steel coil, the process incorporating a leakage flux flaw detecting method in accordance with the present invention.

As shown in FIGS. 13–15, if the above-described leakage flux flaw detecting method in accordance with the present invention is applied to a scaled hot rolled steel sheet or coil, which has so far had difficulty in detecting flaws with high accuracy, and further to a hot rolled steel sheet or coil subjected to descaling treatment (pickling, shot blasting, etc.), since the accurate information of flaw such as location, density, and the like is found beforehand, an engineer in a process subsequent to hot rolling or a customer can take prior measures considering this information. The information of flaw can be provided by means of marking it on the steel sheet or coil, attaching a tag, a sheet, or a recording medium showing it to the steel sheet or coil, and the like.

EXAMPLE 1

The magnetic flaw detector shown in FIG. 5 was provided on a steel sheet inspection line, the steel sheet 1 with a thickness of 1 mm was transferred at a speed of 100 m/min, a magnetic field of 2500 AT was applied to magnetically saturating the steel sheet 1 by the magnetizer 5a (strongly magnetizing condition), and a magnetic field of 1000 AT was applied to make the magnetization of the steel sheet 1 unsaturated by the magnetizer 5b (weakly magnetizing condition). Then, an output signal Va under the strongly magnetizing condition was measured by using the magnetic sensor 6a, and an output signal Vb under the weakly magnetizing condition was measured by using the magnetic sensor 6b. The reason for applying a magnetic field of 2500 AT under the strongly magnetizing condition and applying a magnetic field of 1000 AT under the weakly magnetizing condition is that a common noise signal is measured under both of the conditions and a change in flaw signal level is made larger than a change in noise signal level. The liftoffs L of the magnetic sensors 6a and 6b were set at 0.7 mm. Difference processing was performed in which the output signal Vb multiplied by 2.5 (that is, $K_2$ in the above-described equation (1) is taken as 2.5) is deducted from the output signal Va.

Figure 9:
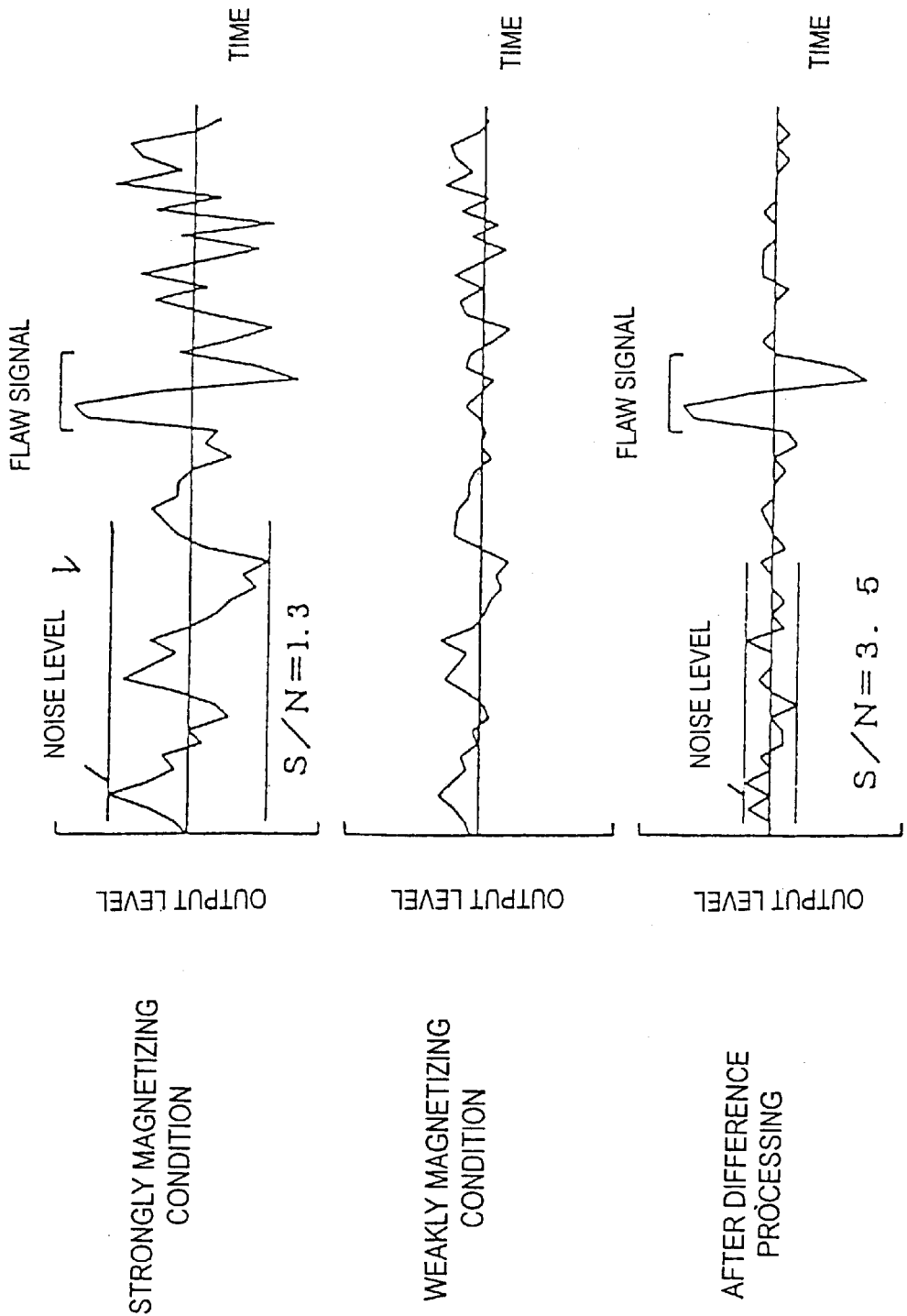
FIG. 9 is a chart showing output signals under various magnetizing conditions and after difference processing.

As shown in FIG. 9, it is found that the S/N ratio of flaw signal obtained under the strongly magnetizing condition has much noise and is as low as 1.3, but the S/N ratio of flaw signal is increased to 3.5 by the difference processing of the output signal obtained under the weakly magnetizing condition.

When measurement is made at the same time over the sheet width by the method of the present invention, the magnetic sensors 6a and 6b must be arranged at given intervals in the sheet width direction. For example, when the magnetic sensors 6a and 6b are provided at intervals of 5 mm for a steel sheet with a width of 1 m, 200 sets of 400 magnetic sensors 6a and 6b are necessary.

EXAMPLE 2

Figure 8:
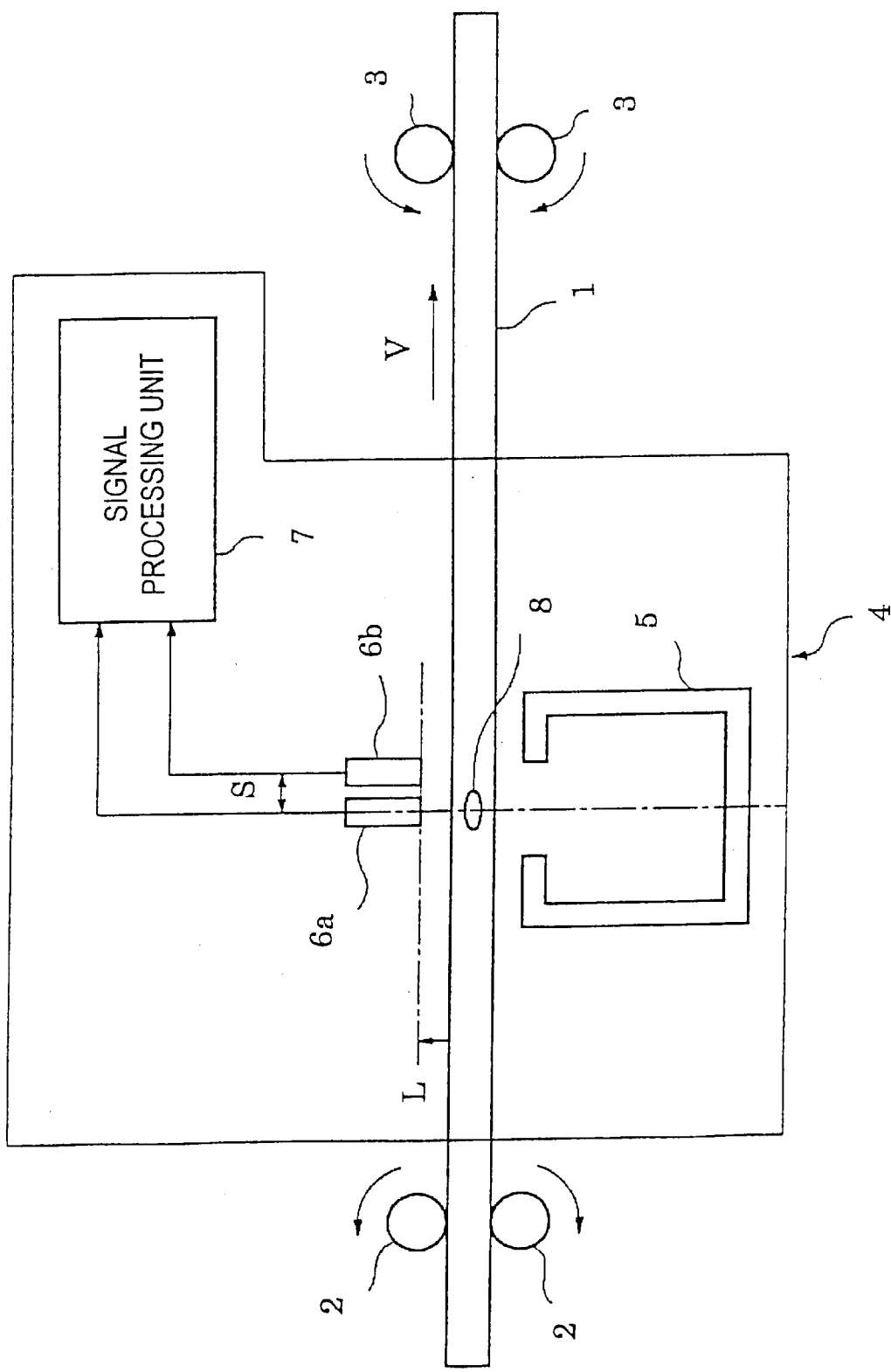
FIG. 8 is a schematic view showing another example of a magnetic flaw detector for carrying out the leakage flux flaw detecting method in accordance with the present invention.

FIG. 8 shows another example of the magnetic flaw detector for carrying out the leakage flux flaw detecting method in accordance with the present invention. In this detector, in addition to the magnetic sensor 6a provided so as to be opposed to the magnetic pole center of the magnetizer 5 of the conventional detector shown in FIG. 1, another magnetic sensor 6b is provided at a position of 4 mm distant from the magnetic sensor 6a in the magnetization direction. The liftoffs L of the magnetic sensors 6a and 6b are set at 0.7 mm.

The magnetic flaw detector shown in FIG. 8 was provided on a steel sheet inspection line, the steel sheet 1 with a thickness of 1 mm was transferred at a speed of 100 m/min, a magnetic field of 3000 AT was applied to magnetically saturate the steel sheet 1 by the magnetizer 5, and the output signal Va corresponding to the strongly magnetizing condition of Example 1 was measured by using the magnetic sensor 6a and the output signal Vb corresponding to the weakly magnetizing condition of Example 1 was measured by using the magnetic sensor 6b. As in the case of Example 1, difference processing in which the output signal Vb multiplied by 2.5 is deducted from the output signal Va was performed. The reason for applying the magnetic field of 3000 AT by using the magnetizer 5 and the magnetic sensor 6b is provided at a position of 4 mm distant from the magnetic sensor 6a in the magnetization direction is that a common noise signal is measured under the strongly magnetizing condition and the weakly magnetizing condition, and a change in flaw signal level is made larger than a change in noise signal level.

As a result, as in the case shown in FIG. 9 obtained in Example 1, although the S/N ratio of flaw signal obtained by the magnetic sensor 6a (corresponding to strongly magnetizing condition) provided at the magnetic pole center of the magnetizer 5 has much noise and is as low as 1.3, the S/N ratio of flaw signal is increased to 3.5 by the difference processing performed on the output signal obtained by the magnetic sensor 6b (corresponding to weakly magnetizing condition) provided at a position of 4 mm distant from the magnetic sensor 6a in the magnetization direction.

Although a case where measurement is made at two magnetization levels is shown in this example, the same is true in a case where a magnetic sensor is provided additionally and measurement is made at three or more magnetization levels. Also, although the magnetic sensors 6a and 6b were disposed on the opposite side of the magnetizer 5 with respect to the steel sheet 1 in this example, the magnetic sensors 6a and 6b and the magnetizer 5 may be disposed on the same side. The direction in which the position of the magnetic sensor is shifted may be the running direction of the steel sheet 1 or may be the direction opposite thereto.

The calculation, delay processing, filtering, and the like of measurement values of the magnetic sensors 6a and 6b may be accomplished with analog signal or may be accomplished after the analog signal is converted into a digital signal. Also, as in the case of Example 1, when measurement is made at the same time over the sheet width by the method of the present invention, the magnetic sensors 6a and 6b must be arranged at given intervals in the sheet width direction.

EXAMPLE 3

Figure 10:
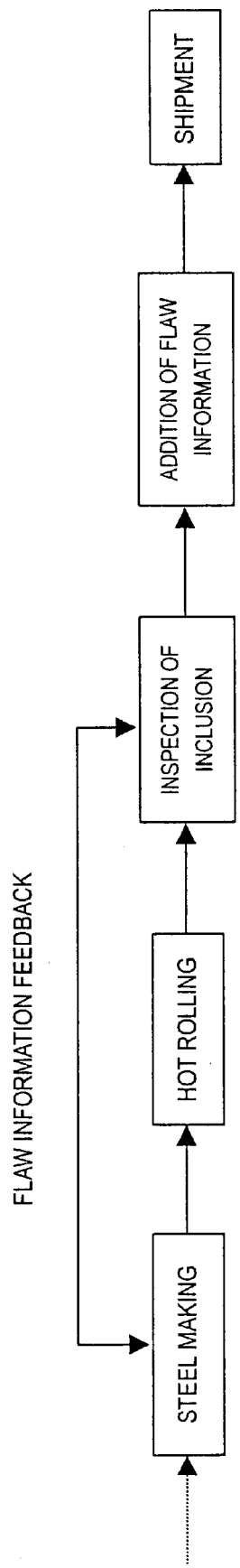
FIG. 10 is a flow diagram showing a manufacturing process for a hot rolled steel sheet, the process incorporating the leakage flux flaw detecting method in accordance with the present invention.

A low carbon hot rolled steel coil with a thickness of 1.8 mm and a width of 1 m was manufactured by a manufacturing process for a hot rolled steel coil incorporating a flaw inspecting process and a flaw information adding process as shown in FIG. 10. A flaw inspection was made in a scaled hot rolled steel coil to obtain the location and density information of flaws. At this time, in the flaw inspecting process, a magnetic flaw detector similar to the detector shown in FIG. 5, in which the magnetic sensors are arranged at intervals of 5 mm in the width direction of coil, was used, and flaws were detected under the same magnetizing conditions as those of Example 1.

Figure 11:
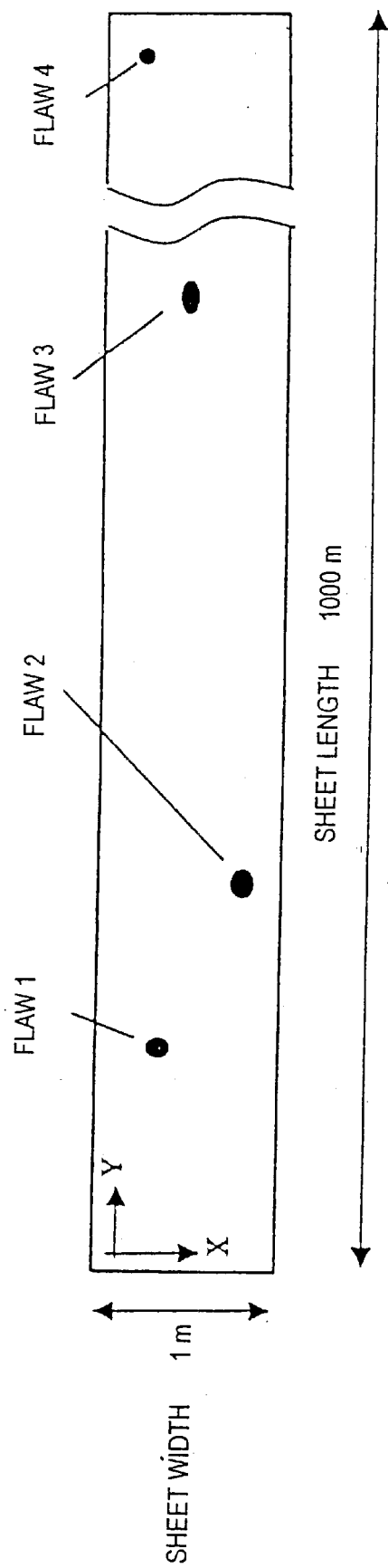
FIG. 11 is a view showing one example of a hot rolled steel coil marked with flaw location information.

FIG. 11 shows an example of some portion of a hot rolled steel coil marked with flaw location over a longitudinal direction of 1000 m. Thus, on a scaled hot rolled steel coil as well, planar location of flaw can be indicated by marking. In addition, at least one of information about the depth, size, or shape of flaw can also be given. Also, more exact information about the location, depth, size, or shape of flaw location can be offered in a form of a sheet as shown in Table 1 or in a form of a recording medium, or can be offered by using information sending means.

Figure 12:
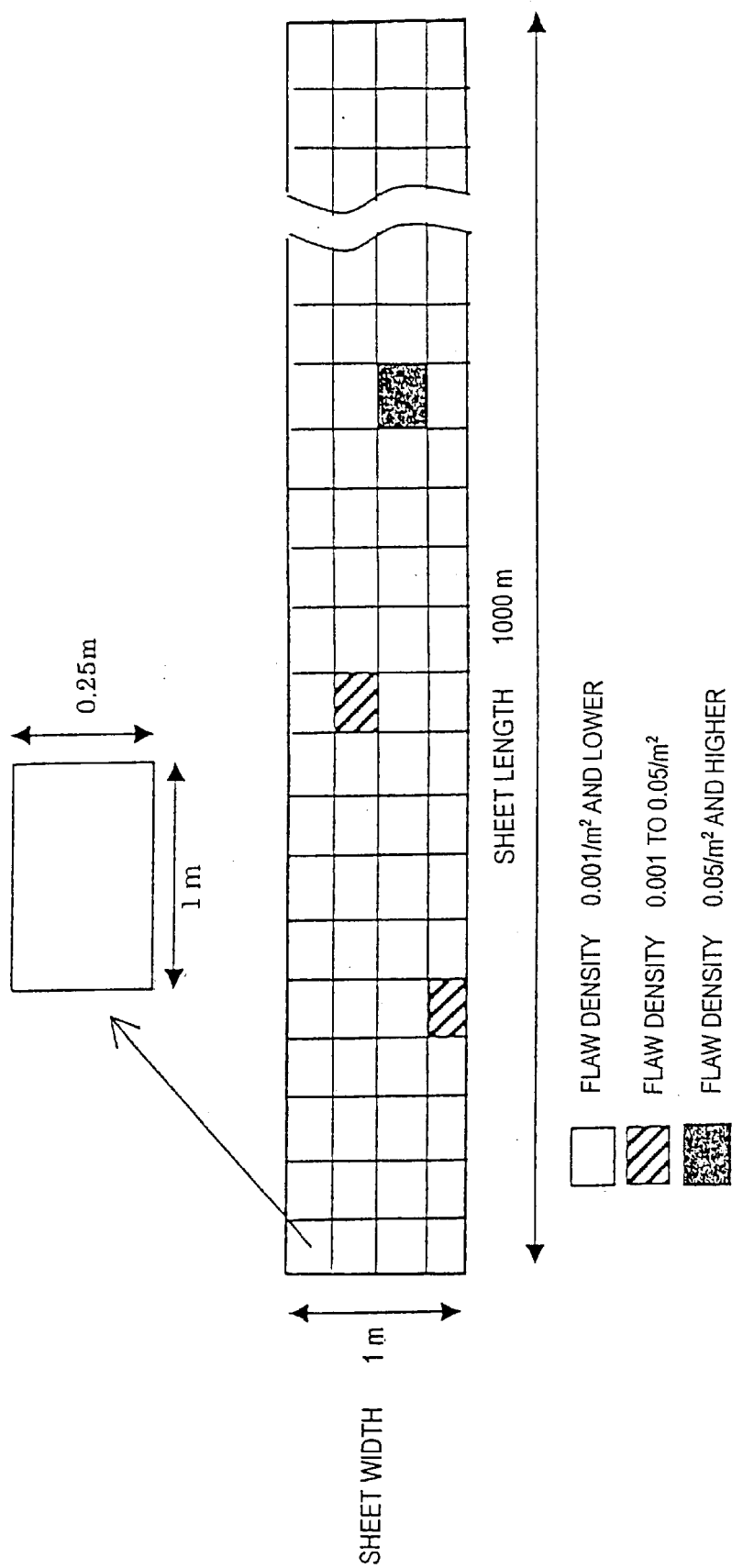
FIG. 12 is a view showing one example of flaw density information determined in the outer peripheral portion of a hot rolled steel coil.

FIG. 12 shows one example of flaw density information in the longitudinal direction of a hot rolled steel coil. Also, the flaw density information on the outer peripheral surface of hot rolled steel coil may be offered.

Besides the hot rolled steel coil, a hot rolled steel coil subjected to descaling treatment (pickling, shot blasting, etc.) which is marked with flaw information or to which flaw information is attached can also be offered.

By the manufacturing method for a hot rolled steel coil and descaled hot rolled steel coil in accordance with the present invention, the flaw information such as location and density as shown in FIGS. 11 and 12 can be given. Therefore, the user of hot rolled steel coil and descaled hot rolled steel coil can make a prior study, for example, can use the coil while avoiding a portion where many flaws are present or can change the purpose of use of the coil, which offers great advantages. Also, as shown in FIG. 10, if the flaw information is fed back to an upstream process, effective data can be supplied for quality control of hot rolled steel coil.

TABLE 1

| Flaw No. | X [m] | Y [m] | Depth position [mm] | Signal level [V] | Area [mm²] | Shape |
|---|---|---|---|---|---|---|
| 1 | 0.3 | 100.3 | 0.34 | 1.2 | 1.0 | Circle |
| 2 | 0.8 | 180.2 | 0.1 | 2.8 | 1.6 | Ellipse |
| 3 | 0.4 | 405.2 | 0.22 | 2.3 | 1.5 | Ellipse |
| 4 | 0.2 | 997.4 | 0.6 | 1.0 | 0.8 | Circle |

What is claimed is:

1. A leakage flux flaw detecting method comprising the steps of:
   magnetizing a ferromagnetic substance successively to a plurality of different intensities of magnetization;
   detecting magnetic flux leaking from the same position of said ferromagnetic substance having been magnetized to each of said intensities of magnetization by using a magnetic sensor; and
   processing output signals of said magnetic sensor corresponding to each of said intensities of magnetization so that a signal caused by a flaw in said ferromagnetic substance is highlighted.

2. The method according to claim 1, wherein the highest intensity of magnetization for magnetizing said ferromagnetic substance is set at the intensity of magnetization at which said ferromagnetic substance is magnetically saturated.

3. The method according to claim 1, wherein the same position of said ferromagnetic substance is successively magnetized to two intensities of magnetization, and an output signal of said magnetic sensor corresponding to the lower intensity of magnetization is deducted from an output signal of said magnetic sensor corresponding to the higher intensity of magnetization by weighting.

4. The method according to claim 3, wherein the higher intensity of magnetization is set at the intensity of magnetization at which said ferromagnetic substance is magnetically saturated.

5. The method according to claim 3, wherein the depth location of flaw from surface is determined by calculating a ratio of an output of said magnetic sensor corresponding to the lower intensity of magnetization to an output of said magnetic sensor corresponding to the higher intensity of magnetization.

6. A leakage flux flaw detecting method comprising the steps of:
   magnetizing a ferromagnetic substance by one or a plurality of magnetizers;
   detecting magnetic flux leaking from the same position of said ferromagnetic substance having been magnetized successively by a plurality of magnetic sensors provided at positions where the intensity of magnetization is different while said ferromagnetic substance is moved along said magnetic sensors; and
   processing output signals of said magnetic sensors so that a signal caused by a flaw in said ferromagnetic substance is highlighted.

7. The method according to claim 6, wherein the intensity of said magnetizer is set so that the higher intensity of magnetization is the intensity of magnetization at which said ferromagnetic substance is magnetically saturated.

8. The method according to claim 6, wherein said magnetic substance is moved along two magnetic sensors provided at positions where the intensity of magnetization is different, and an output signal of said magnetic sensor corresponding to the lower intensity of magnetization at the same position of said ferromagnetic substance is deducted from an output signal of said magnetic sensor corresponding to the higher intensity of magnetization by weighting.

9. The method according to claim 8, wherein the intensity of said magnetizer is set so that the higher intensity of magnetization is the intensity of magnetization at which said ferromagnetic substance is magnetically saturated.

10. The method according to claim 8, wherein the depth location of flaw from surface is determined by calculating a ratio of an output of said magnetic sensor corresponding to the lower intensity of magnetization to an output of said magnetic sensor corresponding to the higher intensity of magnetization.

11. A method for manufacturing a hot rolled steel sheet, comprising the steps of:
    detecting flaws in a hot rolled steel sheet by using the leakage flux flaw detecting method defined in claim 6; and
    determining at least one information of said detected flaws selected from the information of planar location of flaw, the information including planar location and at least one of depth location, size and shape of flaw, and the information of density distribution of flaw.

12. A method for manufacturing a hot rolled steel sheet, comprising the steps of:
    detecting flaws in a hot rolled steel sheet by using the leakage flux flaw detecting method defined in claim 7; and
    determining at least one information of said detected flaws selected from the information of planar location of flaw, the information including planar location and at least one of depth location, size and shape of flaw, and the information of density distribution of flaw.

13. A method for manufacturing a hot rolled steel sheet, comprising the steps of:
    detecting flaws in a hot rolled steel sheet by using the leakage flux flaw detecting method defined in claim 8; and
    determining at least one information of said detected flaws selected from the information of planar location of flaw, the information including planar location and at least one of depth location, size and shape of flaw, and the information of density distribution of flaw.

14. A method for manufacturing a hot rolled steel sheet, comprising the steps of:
    detecting flaws in a hot rolled steel sheet by using the leakage flux flaw detecting method defined in claim 9; and
    determining at least one information of said detected flaws selected from the information of planar location of flaw, the information including planar location and at least one of depth location, size and shape of flaw, and the information of density distribution of flaw.

15. A method for manufacturing a hot rolled steel sheet, comprising the steps of:
    detecting flaws in a hot rolled steel sheet by using the leakage flux flaw detecting method defined in claim 10; and
    determining at least one information of said detected flaws selected from the information of planar location of flaw, the information including planar location and at least one of depth location, size and shape of flaw, and the information of density distribution of flaw.

16. The method according to claim 11, further comprising a step of marking said information of detected flaws on said hot rolled steel sheet.

17. The method according to claim 11, further comprising a step of attaching a tag, a sheet, or a recording medium showing said information of detected flaws to said hot rolled steel sheet.

18. The method according to claim 11, further comprising a step of sending said information of detected flaws to a user of said hot rolled steel sheet.

19. The method according to claim 11, further comprising a step of sending a sheet or a recording medium showing said information of detected flaws to a user of said hot rolled steel sheet.

20. A method for manufacturing a hot rolled steel sheet, comprising the steps of:
   descaling a hot rolled steel sheet;
   detecting flaws in said descaled hot rolled steel sheet by using the leakage flux flaw detecting method defined in claim 6; and
   determining at least one information of said detected flaws selected from the information of planar location of flaw, the information including planar location of flaw and at least one of depth location, size and shape of flaw, and the information of density distribution of flaw.

21. A method for manufacturing a hot rolled steel sheet, comprising the steps of:
   descaling a hot rolled steel sheet;
   detecting flaws in said descaled hot rolled steel sheet by using the leakage flux flaw detecting method defined in claim 7; and
   determining at least one information of said detected flaws selected from the information of planar location of flaw, the information including planar location of flaw and at least one of depth location, size and shape of flaw, and the information of density distribution of flaw.

22. A method for manufacturing a hot rolled steel sheet, comprising the steps of:
   descaling a hot rolled steel sheet;
   detecting flaws in said descaled hot rolled steel sheet by using the leakage flux flaw detecting method defined in claim 8; and
   determining at least one information of said detected flaws selected from the information of planar location of flaw, the information including planar location of flaw and at least one of depth location, size and shape of flaw, and the information of density distribution of flaw.

23. A method for manufacturing a hot rolled steel sheet, comprising the steps of:
   descaling a hot rolled steel sheet;
   detecting flaws in said descaled hot rolled steel sheet by using the leakage flux flaw detecting method defined in claim 9; and
   determining at least one information of said detected flaws selected from the information of planar location of flaw, the information including planar location of flaw and at least one of depth location, size and shape of flaw, and the information of density distribution of flaw.

24. A method for manufacturing a hot rolled steel sheet, comprising the steps of:
   descaling a hot rolled steel sheet;
   detecting flaws in said descaled hot rolled steel sheet by using the leakage flux flaw detecting method defined in claim 10; and
   determining at least one information of said detected flaws selected from the information of planar location of flaw, the information including planar location of flaw and at least one of depth location, size and shape of flaw, and the information of density distribution of flaw.

25. The method according to claim 20, further comprising a step of marking said information of detected flaws on said hot rolled steel sheet.

26. The method according to claim 20, further comprising a step of attaching a tag, a sheet, or a recording medium showing said information of detected flaws to said hot rolled steel sheet.

27. The method according to claim 20, further comprising a step of sending said information of detected flaws to a user of said hot rolled steel sheet.

28. The method according to claim 20, further comprising a step of sending a sheet or a recording medium showing said information of detected flaws to a user of said hot rolled steel sheet.

29. A method for manufacturing a hot rolled steel coil or a descaled hot rolled steel coil, comprising the steps of:
   uncoiling a hot rolled steel coil or a descaled hot rolled steel coil formed by winding a steel sheet into a coil shape;
   detecting flaws in said uncoiled steel sheet by using the leakage flux flaw detecting method defined in claim 6;
   determining at least one information of said detected flaws selected from the information of planar location of flaw, the information including planar location and at least one of depth location, size and shape of flaw, and the information of density distribution of flaw; and
   rewinding said steel sheet into a coil shape.

30. A method for manufacturing a hot rolled steel coil or a descaled hot rolled steel coil, comprising the steps of:
   uncoiling a hot rolled steel coil or a descaled hot rolled steel coil formed by winding a steel sheet into a coil shape;
   detecting flaws in said uncoiled steel sheet by using the leakage flux flaw detecting method defined in claim 7;
   determining at least one information of said detected flaws selected from the information of planar location of flaw, the information including planar location and at least one of depth location, size and shape of flaw, and the information of density distribution of flaw; and
   rewinding said steel sheet into a coil shape.

31. A method for manufacturing a hot rolled steel coil or a descaled hot rolled steel coil, comprising the steps of:
   uncoiling a hot rolled steel coil or a descaled hot rolled steel coil formed by winding a steel sheet into a coil shape;
   detecting flaws in said uncoiled steel sheet by using the leakage flux flaw detecting method defined in claim 8;
   determining at least one information of said detected flaws selected from the information of planar location of flaw, the information including planar location and at least one of depth location, size and shape of flaw, and the information of density distribution of flaw; and
   rewinding said steel sheet into a coil shape.

32. A method for manufacturing a hot rolled steel coil or a descaled hot rolled steel coil, comprising the steps of:
   uncoiling a hot rolled steel coil or a descaled hot rolled steel coil formed by winding a steel sheet into a coil shape;
   detecting flaws in said uncoiled steel sheet by using the leakage flux flaw detecting method defined in claim 9;

determining at least one information of said detected flaws selected from the information of planar location of flaw, the information including planar location and at least one of depth location, size and shape of flaw, and the information of density distribution of flaw; and rewinding said steel sheet into a coil shape.

33. A method for manufacturing a hot rolled steel coil or a descaled hot rolled steel coil, comprising the steps of:

uncoiling a hot rolled steel coil or a descaled hot rolled steel coil formed by winding a steel sheet into a coil shape;

detecting flaws in said uncoiled steel sheet by using the leakage flux flaw detecting method defined in claim 10;

determining at least one information of said detected flaws selected from the information of planar location of flaw, the information including planar location and at least one of depth location, size and shape of flaw, and the information of density distribution of flaw; and rewinding said steel sheet into a coil shape.

34. The method according to claim 29, further comprising a step of marking said information of detected flaws on said hot rolled steel coil or said descaled hot rolled steel coil.

35. The method according to claim 29, further comprising a step of attaching a tag, a sheet, or a recording medium showing said information of detected flaws to said hot rolled steel coil or said descaled hot rolled steel coil.

36. The method according to claim 29, further comprising a step of sending said information of detected flaws to a user of said hot rolled steel coil or said descaled hot rolled steel coil.

37. The method according to claim 29, further comprising a step of sending a sheet or a recording medium showing said information of detected flaws to a user of said hot rolled steel coil or said descaled hot rolled steel coil.

38. A method for manufacturing a descaled hot rolled steel coil, comprising the steps of:

uncoiling a hot rolled steel coil formed by winding a steel sheet into a coil shape;

descaling said uncoiled steel sheet;

detecting flaws in said descaled steel sheet by using the leakage flux flaw detecting method defined in claim 6;

determining at least one information of said detected flaws selected from the information of planar location of flaw, the information including planar location and at least one of depth location, size and shape of flaw, and the information of density distribution of flaw; and rewinding said descaled steel sheet into a coil shape.

39. A method for manufacturing a descaled hot rolled steel coil, comprising the steps of:

uncoiling a hot rolled steel coil formed by winding a steel sheet into a coil shape;

descaling said uncoiled steel sheet;

detecting flaws in said descaled steel sheet by using the leakage flux flaw detecting method defined in claim 7;

determining at least one information of said detected flaws selected from the information of planar location of flaw, the information including planar location and at least one of depth location, size and shape of flaw, and the information of density distribution of flaw; and rewinding said descaled steel sheet into a coil shape.

40. A method for manufacturing a descaled hot rolled steel coil, comprising the steps of:

uncoiling a hot rolled steel coil formed by winding a steel sheet into a coil shape;

descaling said uncoiled steel sheet;

detecting flaws in said descaled steel sheet by using the leakage flux flaw detecting method defined in claim 8;

determining at least one information of said detected flaws selected from the information of planar location of flaw, the information including planar location and at least one of depth location, size and shape of flaw, and the information of density distribution of flaw; and rewinding said descaled steel sheet into a coil shape.

41. A method for manufacturing a descaled hot rolled steel coil, comprising the steps of:

uncoiling a hot rolled steel coil formed by winding a steel sheet into a coil shape;

descaling said uncoiled steel sheet;

detecting flaws in said descaled steel sheet by using the leakage flux flaw detecting method defined in claim 9;

determining at least one information of said detected flaws selected from the information of planar location of flaw, the information including planar location and at least one of depth location, size and shape of flaw, and the information of density distribution of flaw; and rewinding said descaled steel sheet into a coil shape.

42. A method for manufacturing a descaled hot rolled steel coil, comprising the steps of:

uncoiling a hot rolled steel coil formed by winding a steel sheet into a coil shape;

descaling said uncoiled steel sheet;

detecting flaws in said descaled steel sheet by using the leakage flux flaw detecting method defined in claim 10;

determining at least one information of said detected flaws selected from the information of planar location of flaw, the information including planar location and at least one of depth location, size and shape of flaw, and the information of density distribution of flaw; and rewinding said descaled steel sheet into a coil shape.

43. The method according to claim 38, further comprising a step of marking said information of detected flaws on said descaled hot rolled steel coil.

44. The method according to claim 38, further comprising a step of attaching a tag, a sheet, or a recording medium showing said information of detected flaws to said descaled hot rolled steel coil.

45. The method according to claim 38, further comprising a step of sending said information of detected flaws to a user of said descaled hot rolled steel coil.

46. The method according to claim 38, further comprising a step of sending a sheet or a recording medium showing said information of detected flaws to a user of said descaled hot rolled steel coil.

* * * * *